(12) United States Patent
Pearlman et al.

(10) Patent No.: US 10,343,084 B2
(45) Date of Patent: *Jul. 9, 2019

(54) PROCESS FOR SEPARATION OF DIAMINES AND/OR OMEGA-AMINOACIDS FROM A FEED MIXTURE

(71) Applicants: INVISTA NORTH AMERICA S.A.R.L., Wilmington, DE (US); Paul Pearlman, Thornton, PA (US)

(72) Inventors: Paul Pearlman, Thornton, PA (US); Gary Smith, North Yorkshire (GB); Gregory S. Kirby, Avondale, PA (US)

(73) Assignee: INVISTA NORTH AMERICA S.A.R.L., Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 15/564,895

(22) PCT Filed: Apr. 8, 2016

(86) PCT No.: PCT/US2016/026712
§ 371 (c)(1),
(2) Date: Oct. 6, 2017

(87) PCT Pub. No.: WO2016/164767
PCT Pub. Date: Oct. 13, 2016

(65) Prior Publication Data
US 2018/0093200 A1    Apr. 5, 2018

Related U.S. Application Data

(60) Provisional application No. 62/146,129, filed on Apr. 10, 2015.

(51) Int. Cl.
*B01D 15/18* (2006.01)
*C12P 13/00* (2006.01)
(Continued)

(52) U.S. Cl.
CPC ....... *B01D 15/185* (2013.01); *B01D 15/1892* (2013.01); *C07C 209/82* (2013.01);
(Continued)

(58) Field of Classification Search
CPC .................... B01D 15/185; B01D 15/1892
(Continued)

(56) References Cited

U.S. PATENT DOCUMENTS 2,985,589 A    5/1961  Broughton
3,696,107 A   10/1972  Neuzil
(Continued)

FOREIGN PATENT DOCUMENTS

CA         2404442 A1    10/2001
CN      101823928 A  *   9/2010
(Continued)

OTHER PUBLICATIONS

Van Walsem HJ et al: "Simulated moving bed in the production of lysine", Journal of Biotechnology, vol. 59, No. 1-2, Dec. 17, 1997, pp. 127-132. (Year: 1997).*

(Continued)

*Primary Examiner* — Deborah D Carr
(74) *Attorney, Agent, or Firm* — Licata & Tyrrell P.C.; Robert B. Furr, Jr.

(57) ABSTRACT

The present disclosure relates to methods for separating at least one amine chosen from diamines and omega-aminoacids from a feed mixture using a simulated moving bed (SMB) adsorptive technology.

23 Claims, 10 Drawing Sheets

(51) Int. Cl.
*C07C 209/82* (2006.01)
*C07C 209/86* (2006.01)
*C07C 211/09* (2006.01)
*C07C 211/12* (2006.01)
*C07C 213/10* (2006.01)
*C07C 227/38* (2006.01)
*C07C 227/40* (2006.01)
*C07C 229/08* (2006.01)

(52) U.S. Cl.
CPC .......... *C07C 209/86* (2013.01); *C07C 211/09* (2013.01); *C07C 213/10* (2013.01); *C07C 227/38* (2013.01); *C07C 227/40* (2013.01); *C12P 13/001* (2013.01); *C12P 13/005* (2013.01)

(58) Field of Classification Search
USPC ........................................................ 562/554
See application file for complete search history.

(56) References Cited

U.S. PATENT DOCUMENTS

| | | | |
|---|---|---|---|
| 3,706,812 A | 12/1972 | Derosset | |
| 3,761,533 A | 9/1973 | Otani et al. | |
| 4,323,702 A | 4/1982 | Kawabata et al. | |
| 4,333,740 A | 6/1982 | Priegnitz | |
| 4,461,649 A | 7/1984 | Neuzil et al. | |
| 4,483,980 A | 11/1984 | Neuzil et al. | |
| 4,663,048 A | 5/1987 | Tanaka et al. | |
| 4,720,579 A | 1/1988 | Kulprathipanja | |
| 4,764,276 A | 8/1988 | Berry et al. | |
| 4,851,573 A | 7/1989 | Kulprathipanja et al. | |
| 4,851,574 A | 7/1989 | Kulprathipanja | |
| 5,026,482 A | 6/1991 | Sircar | |
| 5,069,883 A | 12/1991 | Matonte | |
| 5,071,560 A | 12/1991 | McCulloch et al. | |
| 5,405,992 A | 4/1995 | Funk et al. | |
| 5,759,406 A | 6/1998 | Phelps et al. | |
| 6,099,654 A * | 8/2000 | Kaneko ................. | C07C 227/28 127/46.2 |
| 6,146,534 A | 11/2000 | Grendze et al. | |
| 6,153,791 A | 11/2000 | Moore | |
| 6,462,221 B1 * | 10/2002 | Gabriel ................. | C07C 213/00 560/22 |
| 6,476,239 B1 | 11/2002 | Arumugam et al. | |
| 6,518,454 B1 | 2/2003 | Arumugam et al. | |
| 6,872,314 B2 | 3/2005 | Boyd et al. | |
| 6,979,402 B1 | 12/2005 | Sprague et al. | |
| 7,166,460 B2 | 1/2007 | Wilkins et al. | |
| 7,241,918 B1 | 7/2007 | Kulprathipanja | |
| 7,820,869 B2 | 10/2010 | Priegnitz et al. | |
| 8,729,298 B2 | 5/2014 | Zang et al. | |
| 9,061,267 B2 | 6/2015 | Gottschall et al. | |
| 9,315,443 B2 | 4/2016 | Erhardt et al. | |
| 2002/0035269 A1 * | 3/2002 | Soper ................... | C07C 227/40 548/339.1 |
| 2003/0094416 A1 * | 5/2003 | Heikkila .............. | B01D 15/185 210/659 |
| 2006/0058555 A1 | 3/2006 | Ostermaier | |
| 2009/0326308 A1 | 12/2009 | Kulprathipanja et al. | |
| 2011/0160483 A1 | 6/2011 | Rezkallah | |
| 2013/0183728 A1 | 7/2013 | Botes et al. | |
| 2013/0210090 A1 | 8/2013 | Pearlman et al. | |
| 2013/0217081 A1 | 8/2013 | Pearlman et al. | |
| 2013/0224807 A1 | 8/2013 | Pearlman et al. | |
| 2014/0046023 A1 | 2/2014 | Gottschall et al. | |
| 2014/0051868 A1 | 2/2014 | Sokolov et al. | |
| 2014/0051888 A1 * | 2/2014 | Dubay .................. | C07C 209/88 564/302 |
| 2014/0186902 A1 | 7/2014 | Botes et al. | |
| 2014/0193865 A1 | 7/2014 | Botes et al. | |
| 2014/0199737 A1 | 7/2014 | Botes et al. | |
| 2014/0242655 A1 | 8/2014 | Pearlrnan et al. | |
| 2014/0248673 A1 | 9/2014 | Botes et al. | |
| 2015/0004660 A1 | 1/2015 | Pearlman et al. | |
| 2016/0159723 A1 | 6/2016 | Smith et al. | |

FOREIGN PATENT DOCUMENTS

| | | | |
|---|---|---|---|
| CN | 101823928 A | 9/2010 | |
| EP | 0324210 A1 | 7/1989 | |
| EP | 0415821 A1 | 3/1991 | |
| EP | 1106602 A1 * | 6/2001 | .......... B01D 15/185 |
| EP | 1106602 A1 | 6/2001 | |
| EP | 2345632 A1 | 7/2011 | |
| EP | 2591773 A2 | 5/2013 | |
| EP | 2591778 A1 | 5/2013 | |
| FR | 2103302 A5 | 4/1972 | |
| FR | 2651148 A1 | 3/1991 | |
| FR | 2651149 A1 | 3/1991 | |
| WO | 2013/005046 A1 | 1/2013 | |
| WO | 2016/164767 A1 | 10/2016 | |

OTHER PUBLICATIONS

Buhlert, "Construction and Development of a New Single-Column Simulated Moving Bed System on the Laboratory Scale", Journal of Chromatography A, 1216, 2009, pp. 8778-8786.
"CHEBI:59758, Gamma-Amino Fatty Acid", available at <http://www.ebi.ac.uk/chebi/searchId.do?chebiId=CHEBI:59758>, last modified on Nov. 7, 2016, 1 page.
"Membrane Filtration Processes Technical Bulletin from TRISEP", available on <https://static1.squarespace.com/static/54e2b7aee4b0902efd671 f90/t/580ff23b2e69cf6ad153bd42/1477440060214/TB- 025+Membrane+Filtration+Processes+-+Dead-End>, Jun. 9, 2016, pp. 1-2.
Wikipedia, "Simulated Moving Bed", available at <https://en.wikipedia.org/wiki/Simulated_moving_bed>, last edited on May 5, 2017, 3 pages.
International Preliminary Report on Patentability issued in International Application No. PCT/US2016/026712, dated Oct. 19, 2017, 10 pages.
International Search Report and Written Opinion received for PCT Patent Application No. PCT/US2016/026712, dated Jun. 21, 2016, 12 pages.
Van Walsem, et al., "Simulated Moving Bed in the Production of Lysine", Journal of Biotechnology, Elsevier Science Publishers, vol. 59, 1997, pp. 127-132.
U.S. Non-Final Office Action issued in copending U.S. Appl. No. 15/094,770, filed Apr. 8, 2016, dated Jun. 15, 2017, 36 pages.
Notice of Allowance received in copending U.S. Appl. No. 15/094,770, filed Apr. 8, 2016, dated Nov. 30, 2016, 4 pages.
Notice of Allowance received in copending U.S. Appl. No. 15/094,770, filed Apr. 8, 2016, dated Oct. 28, 2016, 8 pages.
International Preliminary Report on Patentability in PCT/US2016/026712 dated Oct. 10, 2017.
Office communication dated Mar. 13, 2018 from U.S. Appl. No. 15/094,770, filed Apr. 8, 2016.
Office communication dated Jan. 3, 2019 from U.S. Appl. No. 15/094,770, filed Apr. 8, 2016.

* cited by examiner

PROCESS FOR SEPARATION OF DIAMINES AND/OR OMEGA-AMINOACIDS FROM A FEED MIXTURE

This application is the U.S. National Stage of International Application No. PCT/US2016/026712 filed Apr. 8, 2016, which claims priority to U.S. provisional application No. 62/146,129, filed on Apr. 10, 2015, each of which is herein incorporated by reference in its entirety.

FIELD OF THE DISCLOSURE

The present disclosure relates to methods for separating at least one amine chosen from diamines and omega-aminoacids (i.e., ω-aminoacids) from a feed mixture using a simulated moving bed (SMB) adsorptive technology.

SUMMARY OF THE DISCLOSURE

Diamines and/or ω-aminoacids can be used as monomers for synthesizing a variety of materials such as polyimide resins and fibers. For instance, hexamethylenediamine (HMD, a.k.a., 1,6-hexanediamine), a diamine, is a chemical intermediate used in the production of nylon 6,6 via a condensation reaction with adipic acid. HMD is also used in the production of epoxy resins as well as the production of monomers for polyurethanes. 7-aminoheptanoic acid (7-AHA), an ω-aminoacid, has been used in the manufacture of nylon 7.

Commercial quantities of diamines or ω-aminoacids can be prepared via chemical methods. For example, a process of producing HMD comprises the steps of subjecting butadiene to a hydrocyanation process in the presence of nickel catalyst to produce adiponitrile, and hydrogenating adiponitrile in the presence of a solid catalyst to yield HMD. At the end of that process, HMD needs to be separated from a mixture comprising 6-aminocapronitrile, HMD, tetrahydrozaepine, adiponitrile, and low boilers via, for example, by methods involving fractional distillation. See e.g., U.S. Patent Application No. 2006/0058555.

Further as an example, 7-AHA may be synthesized by reacting 7-bromo-heptanoic acid with concentrated aqueous ammonia. That reaction may result in a mixture comprising ammonium bromide and 7-AHA, which can be separated by using ion-exchange resins.

A biological process such as fermentation process may be used to produce at least one amine chosen from diamines and ω-aminoacids. For example, U.S. Patent Application Publication Nos. 20130183728, 20130210090, 20130217081, 20130224807, 20140186902, 20140242655, 20150004660, and 2014/0199737 discloses biochemical pathways for producing HMD by forming one or two terminal functional groups, comprised of carboxyl, amine or hydroxyl group, in a C6 aliphatic backbone substrate; and U.S. Patent Application Publication Nos. 20140193865 and 20140248673 discloses biochemical pathways for producing 7-AHA by forming two terminal functional groups, comprised of carboxyl, amine or hydroxyl group, in a C7 aliphatic backbone substrate.

Biological processes, however, frequently suffer from several limitations including 1) a relatively small range of products; 2) low yields, titers, and productivities; and 3) difficulty recovering and purifying products from aqueous solutions. In particular, during the recovery step, techniques such as distillation, decantation, extraction, pervaporation, and chromatography have been employed. These methods, however, may be energy intensive, expensive to operate, and not practical or economical for the recovery and purification of materials from, for example, a fermentation broth.

Commercial applications of diamines and ω-aminoacids may require them to be of very high purity with low quantities of impurities. Accordingly, it would be beneficial to be able to separate diamines and/or ω-aminoacids produced in, for example, a commercial scale biological process in a simple and low-cost way.

The present disclosure provides methods for separating at least one amine chosen from diamines and ω-aminoacids from a multi-component mixture, such as a fermentation product, using a simulated moving bed (SMB) adsorptive technology.

SMB apparatuses suitable for separating the at least one amine from a feed mixture may comprise one or more separation zones. For example, a SMB may comprise only one zone to separate a desired product component from other impurities when all of those impurities elute either faster or slower than the desired product component. Further as an example, a SMB apparatus may comprise more than one separation zone, and the components separated in each zone may have different polarities.

In one aspect, each zone may contain: one or more injection points for a feed mixture; one or more injection points for an eluent, the eluent comprising, for example, an aqueous alcohol; a take-off point for an extract stream; and a take-off point for a raffinate stream. In one aspect, part of the extract and/or raffinate streams can be recycled back into the same zone, and for example, the eluent and/or recycle stream may be adjusted such that the diamines and/or ω-aminoacids can be separated from different components of the feed mixture each zone.

The present disclosure also relates to compositions comprising diamines and/or ω-aminoacids, such as provided by the separation method disclosed herein.

Definitions

While mostly familiar to those versed in the art, the following definitions are provided in the interest of clarity.

"Zone" refers to a system capable of accomplishing a binary separation comprising: a plurality of chromatography columns, one or more injection points for a feed mixture stream, one or more injection points for one or more eluents, a raffinate take-off stream from which liquid can be collected from the plurality of chromatography columns, and an extract take-off stream from which liquid can be collected from the plurality of chromatography columns. In one aspect, each zone has only one injection point for a feed stream. In another aspect, each zone has only one injection point for an eluent. In yet another aspect, each zone has two or more injection points for different eluent.

"Raffinate" is the stream of components that move more rapidly with the liquid eluent phase compared with the solid adsorbent phase. As an example, a raffinate stream can be enriched with more polar components, and depleted of less polar components compared with a feed stream.

"Extract" is the stream of components that move more rapidly with the solid adsorbent phase compared with the liquid eluent phase. As an example, an extract stream can be enriched with less polar components, and depleted of more polar components compared with a feed stream.

"Nonadjacent" when applied to columns in the same apparatus refers to columns separated by one or more columns, such as 3 or more columns, further such as 5 or more columns.

"SMB" means simulated moving bed adsorptive technology.

DETAILED DESCRIPTION OF CERTAIN ASPECTS

Figure 1:
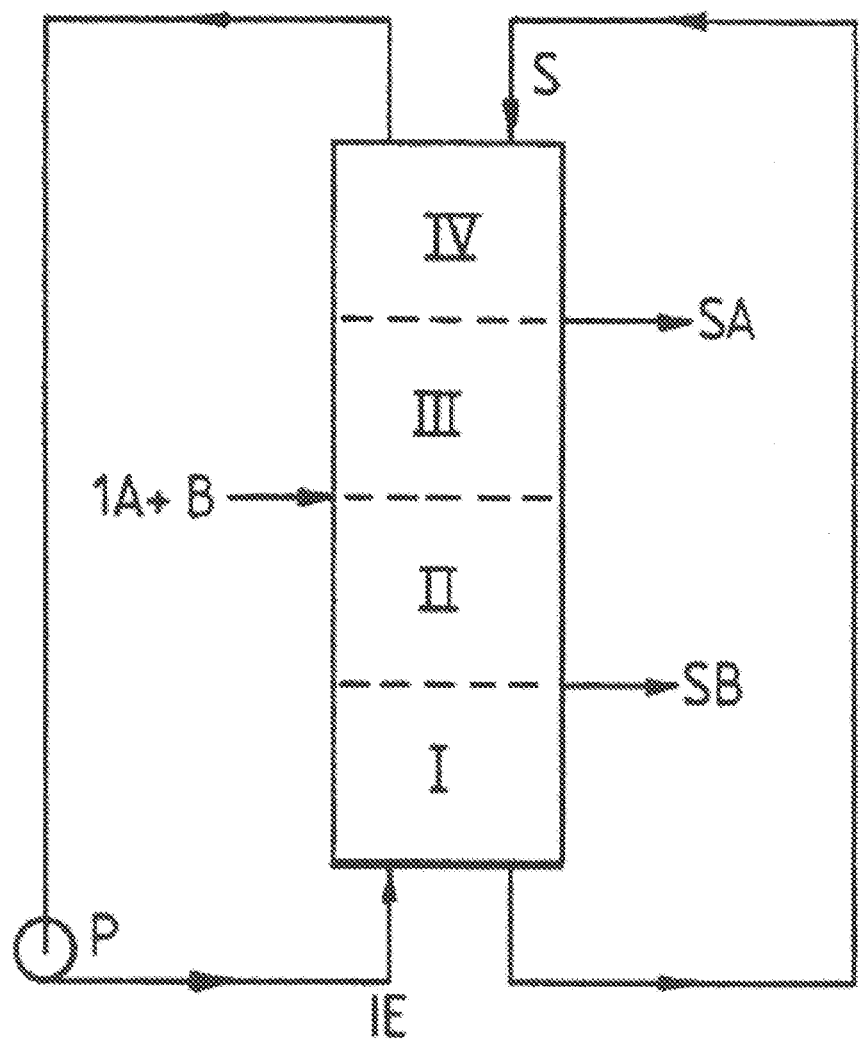
FIG. 1 illustrates an exemplary SMB process for separating a binary mixture.

According to certain aspects, the present disclosure provides method for separating at least one amine chosen from diamines and ω-aminoacids from a feed mixture.

In some aspects, the at least one amine may be chosen from C3-C12 diamines and ω-aminoacids. In some aspects, the at least one amine may be linear or branched. As a non-limiting example, the at least one amine may be chosen from C5-C8 linear aliphatic α, ω-diamines, and ω-aminoacids. In some aspects, the diamine is selected from pentamethylenediamine, hexamethylenediamine, heptamethylenediamine, and 1,12-diaminododecane As a non-limiting example, the diamine may be hexamethylenediamine (HMD, a.k.a., 1,6-hexanediamine, CAS #124-09-4). In some aspects, the ω-aminoacid is an omega-aminocarboxylic acid, and in yet some aspects, the ω-aminoacid is selected from 5-aminopentaoic acid, 6-aminocaporic acid, 7-aminoheptanoic acid, 11-aminounidecanoic acid, or 12-aminolauric acid. Further as a non-limiting example, the ω-aminoacid may be 7-aminoheptanoic acid (7-AHA, CAS #929-17-9).

In some aspects, the diamines and/or ω-aminoacids may be produced directly by a microorganism under suitable fermentation conditions. In some aspects, the at least one amine may be produced indirectly by microorganism. For example, the microorganism may produce an intermediate component, which may subsequently be subject to one or more processing steps to produce the desired diamine and/or ω-aminoacid such as HMD or 7-AHA.

In some aspects, the feed mixture comprising at least one amine chosen from diamines and ω-aminoacids is an aqueous mixture.

In some aspects, the feed mixture comprising at least one amine chosen from diamines and ω-aminoacids may be from a chemical process such as a petrochemical process.

In some aspects, the feed mixture comprising at least one amine chosen from diamines and ω-aminoacids may be from a biological process. For example, the feed mixture may be produced from one or more processes chosen from fermentation, biomass extraction, biocatalytic, and enzymatic processes.

In some aspects, the feed mixture may be produced from a combined chemical and biological process.

Fermentation Product

According to certain aspects, the processes disclosed in the present disclosure may be adaptable to a variety of biofermentation processes, for example, those suitable for large-scale industrial processes. In some aspects, the fermentation product comprising at least one amine chosen from diamines and ω-aminoacids may be produced by batch, fed-batch, and/or continuous biofermentation.

Classical batch biofermentation is a closed system where the composition of the broth is set at the beginning of the biofermentation and not subjected to artificial alterations during the biofermentation. Thus, at the beginning of the biofermentation the broth is inoculated with the desired microorganism or organisms and biofermentation proceeds without further addition to the system. Typically, however, "batch" biofermentation is batch with respect to the addition of carbon source and attempts are often made at controlling factors such as pH and oxygen concentration. In batch systems the metabolite and biomass compositions of the system change constantly up to the time the biofermentation is stopped. Within batch cultures cells moderate through a static lag phase to a high-growth log phase and finally to a stationary phase where growth rate is diminished or halted. If untreated, cells in the stationary phase will eventually die. Cells in log phase generally are responsible for the bulk of production of end product or intermediate, when the product is growth associated.

Fed-batch biofermentation processes comprise a typical batch system with the exception that the substrate is added in increments as the biofermentation progresses. Fed-batch systems are useful when catabolite repression is apt to inhibit the metabolism of the cells and where it is desirable to have limited amounts of substrate in the media.

In a continuous biofermentation system, a defined biofermentation solution is added continuously to a bioreactor and an equal amount of biofermentation solution is removed simultaneously for processing. Continuous biofermentation generally maintains the cultures at a constant high density where cells are primarily in log phase growth. The methodology allows modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to operate under steady state growth conditions and balance cell loss due to biofermentation solution being drawn off against cell growth rate in the biofermentation.

Materials and methods known to those skilled in the art of microbiology or biofermentation science may be adapted for generating a fermentation product comprising at least one amine chosen from diamines and ω-aminoacids.

In some embodiment, the fermentation product can be produced by prokaryote host, eukaryote host, or both. The prokaryotic host can be, as non-limiting examples, from the genus *Escherichia* such as *Escherichia coli*; from the genus *Clostridia* such as *Clostridium ljungdahlii, Clostridium autoethanogenum*, or *Clostridium kluyveri*; from the genus *Corynebacteria* such as *Corynebacterium glutamicum*; from the genus *Cupriavidus* such as *Cupriavidus necator* or *Cupriavidusmetallidurans*; from the genus *Pseudomonas* such as *Pseudomonas fluorescens, Pseudomonas putida* or *Pseudomonas oleavorans*; from the genus *Delftia acidovorans*, from the genus *Bacillus* such as *Bacillus subtillis*; from the genes *Lactobacillus* such as *Lactobacillus delbrueckii*; from the genus *Lactococcus* such as *Lactococcus lactis*; or from the genus *Rhodococcus* such as *Rhodococcus equi*. The eukaryotic host can be, as non-limiting examples, from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica* or from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*.

In some embodiments, the fermentation product disclosed herein can be produced by *Cupriavidus necator* (*C. necator*).

In some aspects, the methods disclosed in U.S. Patent Application Publication Nos. 20130183728, 20130210090, 20130217081, 20130224807, 20140186902, 20140242655, 20150004660, and 2014/0199737 may be used for generating a fermentation product comprising HMD.

In some aspects, the methods disclosed in U.S. Patent Application Publication Nos. 20140193865 and 20140248673 may be used for generating a fermentation product comprising 7-AHA.

"Fermentation broth" refers to an aqueous solution produced directly from batch, fed-batch, and/or continuous biofermentation vessel. The fermentation broth may comprise microorganisms, at least one amine chosen from diamines and ω-aminoacids, metabolic intermediates, and other components such as salts, vitamins, amino acids, cofactors, and antibiotics.

In some aspects, the fermentation broth may be directly fed to a SMB for separation of the at least one amine. In that case, the fermentation product fed into the SMB is the fermentation broth.

In some aspects, the fermentation broth may be subject to one or more treatments, such as solid-liquid separation, prior to being fed into a SMB.

Various solid-liquid separation methods may be used to treat fermentation broth to product a fermentation product comprising at least one amine chosen from diamines and ω-aminoacids. As non-limiting examples, cross-flow filtration, centrifugation, and/or dead-end filtration may be used to treat the fermentation broth to produce a fermentation product comprising the at least one amine.

In one exemplary aspect, the fermentation broth may be subject to a cross-flow filtration unit that separates an influent stream into two effluent streams. The effluent that passes through a membrane is a biomass-free solution (or permeate) comprising at least one amine chosen from diamines and ω-aminoacids. The other effluent stream (or retentate) rejected by the membrane contains the cellular material of the biomass and the supernatant. This second biomass-containing effluent stream may be immediately returned to a fermentation vessel.

Membrane suitable for cross-flow filtration depends on the size of the particles to be removed from the influent stream. In one aspect, membranes with pore sizes about 0.2 micron and smaller, generally used for microfiltration and ultrafiltration, may be used. Further as non-limiting examples, membranes comprising cellulosic, polyamide, polysulfone, and/or polyvinylidene fluoride may also be suitable for cross-flow filtration.

In addition to membrane selection, the combined effects of temperature, pressure, and contaminant fouling may need to be carefully considered to ensure successful operation of a cross-flow filtration unit. The chemical compatibility and membrane stability at a given process stream pH may constitute additional factors to be considered. These conditions may be optimized readily by one skilled in the art.

In some aspects, the fermentation product that has been treated with a solid-liquid separation may be optionally subject to one or more filtration steps. As a non-limiting example, the fermentation product, before being subjected to SMB, may be fed into a second stage cross-flow filtration unit with more selective membranes or smaller pore sizes. This optional filtration would remove other components from the biocatalyst-free solution, such as proteins, protein fragments, divalent salts, monovalent ions, or organics. Using a second stage filtration unit may potentially increase the life of the chromatographic adsorbent.

In some aspects, the fermentation product that will be fed into a SMB apparatus may comprise at least one amine chosen from diamines and/or ω-aminoacids and at least one more polar component or at least one less polar component than the at least one amine. The less polar components may have a stronger adherence to the adsorbent used as compared to the desired diamines and/or ω-aminoacids product. During operation, such less polar components may move with the solid adsorbent phase in preference to the liquid eluent phase. The more polar components have a weaker adherence to the adsorbent used in the method of the present disclosure than does the diamines and/or ω-aminoacids product. During operation, such more polar components may move with the liquid eluent phase in preference to the solid adsorbent phase. In some aspects, more polar components will be separated into a raffinate stream, and less polar components will be separated into an extract stream.

Examples of the more and less polar components include (1) other compounds from the manufacturing process (for example, other unwanted diamines and/or ω-aminoacids, hydroxylated fatty acids, fatty acids, fatty acid esters, hydrocarbons, diacids, ω-hydroxyamines, or hydroxycarboxylic acids), (2) byproducts formed during storage, refining and previous concentration steps, and (3) contaminants from solvents or reagents which are utilized during previous concentration or purification steps.

Simulated Moving Bed (SMB)

A simulated moving bed (SMB) system suitable for separating at least one amine from a feed mixture may comprise one zone or more than one zone. For example, a SMB may comprise only one zone to separate a desired product component from other impurities when all of those impurities elute either faster or slower than the desired product component. Further as an example, a SMB apparatus may comprise more than one separation zone, and the components separated in each zone may have different polarities, or different affinities for a particular stationary phase or particular eluent. Each zone comprises a plurality of chambers or columns, each of which contains a bed of solid adsorbent or mixture of solid adsorbents. Each zone may further comprise one or more injection points for a feed mixture; one or more injection points for an eluent, the eluent comprising, for example, an aqueous alcohol; a take-off point for an extract stream; and a take-off point for a raffinate stream.

A zone can be broken down into sub-zones (also called sections in FIG. 1) where the columns in that sub-zone perform a particular portion of the separation, for example, adsorb A from feed, desorb B from the solid adsorbent into eluent, etc.

The SMB may comprise one separation zone or a plurality of separation zones and may be further equipped with a plurality of inlet and outlet ports. For example, a SMB may comprise only one zone to separate a desired product component from impurities when all of those impurities either elute faster than or elute slower than the desired product component. Further as an example, a SMB apparatus may comprise more than one separation zone, and the components separated in each zone may have different polarities.

The columns used in a SMB may be packed with a solid or mixture of solids having different adsorptivities for organic compounds and, thus, may be effective for separating at least one amine chosen from diamines and ω-aminoacids from other compounds by selective adsorption. The SMB may be equipped with a rotary valve or a plurality of valves arranged in a manner such that any feed stream may be introduced to any section or zone, and any outlet or effluent stream may be withdrawn from any section or zone.

During operation of the SMB, the inlet connections to which the feed streams are fed and the outlet connections from which the outlet streams are withdrawn may be periodically moved, or indexed, from their respective columns to adjacent columns. For example, in one aspect, to achieve separation of at least one amine chosen from diamines and ω-aminoacids, the locations of the inlet and outlet streams may be moved intermittently, from column to the next adjacent column, in the direction of liquid eluent flow. The intermittent port movement in the direction of liquid eluent flow simulates the counter-current movement of the bed or beds of the solid adsorbent. Different equipment and operational strategies may be used to simulate the counter-current movement of the solid with respect to the liquid.

Any known simulated or actual moving bed chromatography apparatus may be utilized for the purposes of separating of diamines and ω-aminoacids from a feed mixture such as a fermentation product. As non-limiting examples, apparatuses described in U.S. Pat. Nos. 2,985,589, 3,696,107, 3,706,812, 3,761,533, FR-A-2103302, FR-A-2651148, FR-A-2651149, U.S. Pat. Nos. 6,979,402, 5,069,883 and 4,764,276, the contents of which are herein incorporate by reference in their entirety, may be configured and operated, according to the present disclosure, for separating of diamines and/or ω-aminoacids from a feed mixture such as a fermentation product.

An exemplary process of separating at least one amine from a feed mixture may be demonstrated via a process of separating a binary mixture in a single zone system illustrated in FIG. 1. A vertical chromatographic column containing stationary phase S may be divided into sections, such as into four superimposed sub-zones I, II, III and IV going from the bottom to the top of the column. The eluent is introduced at the bottom at IE by means of a pump P. The mixture of the components A and B which are to be separated is introduced at IA+B between sub-zone II and sub-zone III. An extract containing mainly B is collected at SB between sub-zone I and sub-zone II, and a raffinate containing mainly A is collected at SA between sub-zone III and sub-zone IV.

In the case of a simulated moving bed system, a simulated downward movement of the stationary phase S is caused by movement of the introduction and collection points relative to the solid phase. In the case of an actual moving bed system, downward movement of the stationary phase S is caused by movement of the various chromatographic columns relative to the introduction and collection points. In FIG. 1, eluent flows upward and mixture A+B is injected between sub-zone II and sub-zone III. The components will move according to their chromatographic interactions with the stationary phase, for example adsorption on a porous medium. The component B that exhibits stronger affinity to the stationary phase (the slower running component) will be more slowly entrained by the eluent and will follow it with delay. The component A that exhibits the weaker affinity to the stationary phase (the faster running component) will be easily entrained by the eluent. If the right set of parameters, especially the flow rate in each zone, are correctly estimated and controlled, the component A exhibiting the weaker affinity to the stationary phase will be collected between subzone III and sub-zone IV as a raffinate and the component B exhibiting the stronger affinity to the stationary phase will be collected between sub-zone I and sub-zone II as an extract.

Adsorbents

Each chamber or column present in a SMB system comprises one or more adsorbents having different adsorptivities for diamines and/or ω-aminoacids. The terms "adsorption" or "adsorptivity", as used herein, are intended to have the commonly understood meanings by persons skilled in the art, i.e., the tendency or affinity of gases, liquids, or solutes to accumulate on the surface of a solid or adsorbent. Similarly, terms "adsorbent", "solid adsorbent", and "stationary phase", as used herein in regards the adsorbent material contained within a SMB or other chromatographic system, are intended to be synonymous and are used interchangeably.

The adsorbent or adsorbents used in the SMB may be selected on the basis of the at least one amine to be separated, the amount of water and solvents present, the desorbent, components present in the feed mixture, and the desired separation.

In some aspects, more than one type of adsorbent may be used in the SMB. For example, the SMB may be packed with a mixture, such as a uniform or homogenized mixture, of two or more solid materials. As another example, different adsorbent materials may be packed in different locations/columns/sub-zones/zones of the SMB. As another example, the SMB could use multiple adsorbents both as a mixture of adsorbents and in different locations within the SMB.

In one aspect, each chromatographic column in the SMB contains the same adsorbent. In another aspect, each chromatographic column in the SMB contains different adsorbents. In yet another aspect, when the SMB contains multiple zones, chromatographic columns within a zone may contain the same or different adsorbents. For example, each column in zone 1 may contain the same type of adsorbent that is different from the adsorbent contained in zone 2. Further as an example, each column in zone 1 may contain different types of adsorbent, but the same types of adsorbent may be similarly used in different columns of zone 2.

Examples of suitable adsorbents include activated carbon, floridin, diatomite, molecular sieves, alumina, silica, silica-alumina, titania, polymeric resins containing one or more groups selected from sulfonate, hydroxy, amino, halogen, pyridyl, mono-substituted amino, disubstituted amino, acyl, acyloxy, keto, alkoxy, and polymeric resins containing immobilized silver or lead, commonly known as immobilized metal affinity columns (abbreviated herein as "IMAC"). Further examples of adsorbents are Amberlite® XAD-4, XAD-7, and XAD-8 resins, available from Rohm & Haas Co.

In some aspects, the adsorption resin can be chosen from macroporous adsorption resins. For example, the macroporous adsorption resin can be chosen from nonpolar macroporous adsorption resins such as DOW XAD/4/8. Further as an example, the macroporous adsorption resin can be chosen from polar macroporous adsorption resins. In some aspects, the stationary phase comprises adsorption resin and at least one material chosen from activated carbon, floridin, diatomite and silica gel. In some aspects, the stationary phase is Orpheus silica-based stationary phase adsorbent (manufactured by Orochem Technologies Inc., Naperville, Ill., USA).

The shape of the adsorbent material can be, for example, spherical or nonspherical beads. In some aspects, the adsorbent material can be substantially spherical beads. Such beads can have a diameter of from 20 to 500 microns, for example from 20 to 400 microns, from 30 to 3500 microns, from 40 to 300 microns, from 50 to 250 microns, from 1000 to 400 microns, or from 250 to 350 microns. In some circumstances, larger particles may enable a lower pressure of eluent to be used in the system. This, in turn, has advantages in terms of cost savings, efficiency and lifetime of the apparatus.

In some aspects, the adsorbent can have a pore size of from 1 to 200 nm, 2 to 150 nm, from 3 to 140 nm, from 4 to 130 nm, from 5 to 120 nm, 10 to 120 nm, from 6 to 50 nm, from 15 to 45 nm, from 20 to 40 nm, from 25 to 35 nm, from 6 to 20 nm, from 7 to 12 nm, or from 8 to 11 nm.

Eluent

The SMB may contain one or more eluents (desorbent) that are liquid or solvent(s) capable of displacing a selectively adsorbed organic compound from the adsorbent. The eluent may be a single solvent or a mixture of solvents. For example, the eluent may comprise at least one solvent chosen from water, alcohols, dials, esters, nitriles, ketones, and ethers.

In one aspect, the desorbent may be a straight- or branched-chain, unsubstituted or substituted alcohol, diol, ester, nitrile, ketone, or ether containing up to about 10 carbon atoms. Non-limiting examples of desorbents may include methanol, ethanol, propanol, isopropanol, and butanol; dials, such as ethylene glycol, 1,3-propanediol, 1,2-propanediol, and 1,4-butanediol; nitriles, such as acetonitrile and butyronitrile; ketones, such as acetone, methyl ethyl ketone, and diethyl ketone; esters, such as methyl acetate, ethyl acetate, methyl propionate, and butyl acetate; and aliphatic and cyclic ethers, such as dimethyl ether, tetrahydrofuran, and dioxane.

In some aspects, the eluent can be an aqueous alcohol. The aqueous alcohol can comprise water and one or more short chain alcohols. The short chain alcohol can have from 1 to 6 carbon atoms. Non-limiting examples of suitable alcohols include methanol, ethanol, n-propanol, i-propanol, n-butanol, i-butanol, s-butanol and t-butanol. In one exemplary aspect, methanol and ethanol can be used. In yet another exemplary aspect, methanol can be used.

In some aspects, the average water:alcohol ratio of the eluent in the entire apparatus can be from 0.1:99.9 to 95:5 parts by volume, for example from 0.1:99.9 to 9:91 parts by volume, from 0.2:99.8 to 7:93 parts by volume, from 0.5:99.5 to 6:94 parts by volume, from 5:95 to 20:80 parts by volume, from 50:50 to 95:5 parts by volume, from 30:70 to 70:30 parts by volume, or from 30:70 to 50:50 parts by volume.

In some aspects where SMB contain more than one zone, the eluting power of the eluent in each of the zones can be different. For example, the eluting power of the eluent in the first zone can be greater than that of the eluent in the second and subsequent zones. In practice this can be achieved by varying the relative amounts of water and alcohol in each zone. Alcohols are generally more powerful desorbers than water. Thus, the amount of alcohol in the eluent in the first zone can be greater than the amount of alcohol in the eluent of the second and subsequent zones.

In some aspects, where the aqueous alcohol present in each zone has a different water alcohol content, the water:alcohol ratio of the eluent in the first zone can be from 0:100 to 5:95 parts by volume, for example from 0.1:99.9 to 2.5:97.5 parts by volume, from 0.2:99.8 to 2:98 parts by volume, or from 0.5:99.5 to 1.5:98.5 parts by volume. Additionally, the water:alcohol ratio of the eluent in the second zone can be from 3:97 to 7:93 parts by volume, from 4:96 to 6:94 parts by volume, or from 4.5:95.5 to 5.5:94.5 parts by volume.

In one exemplary aspect, where the aqueous alcohol present in each zone has a different water alcohol content, the water:alcohol ratio of the eluent in the first zone can be from 0.5:99.5 to 1.5:98.5 parts by volume, and the water:alcohol ratio of the eluent in the second zone can be from 4.5:95:5 to 5.5:94.5 parts by volume.

In some aspects where the rate at which liquid collected via the extract and raffinate streams in each zone is recycled back into the same zone is adjusted such that diamines and/or ω-aminoacids can be separated from different components of the feed mixture in each zone, the water:alcohol ratio of the eluents in each zone can be the same or different. For example, the water:alcohol ratio of the eluent in each zone can be from 0.5:99.5 to 5.5:94.5 parts by volume. Further as an example, the water:alcohol ratio of the eluent in the first zone can be lower than the water:alcohol ratio of the eluent in the second zone. Further as another example, the water:alcohol ratio of the eluent in the first zone can be higher than the water:alcohol ratio of the eluent in the second zone. Also further as an example, the water:alcohol ratio of the eluent in the first zone can be the same as the water:alcohol ratio of the eluent in the second zone.

In some aspects, the ratios of water and alcohol in each zone referred to above are average ratios within the totality of the zone.

In some aspects, the water:alcohol ratio of the eluent in each zone can be controlled by introducing water and/or alcohol into one or more columns in the zones. Thus, for example, to achieve a lower water:alcohol ratio in the first zone than in the second zone, water can be introduced more slowly into the first zone than the second zone. In another example, essentially pure alcohol and essentially pure water can be introduced at different points in each zone. The relative flow rates of these two streams will determine the overall solvent profile across the zone. In yet another example, different alcohol/water mixtures can be introduced at different points in each zone. That will involve introducing two or more different alcohol/water mixtures into the zone, each alcohol/water mixture having a different alcohol:water ratio. The relative flow rates and relative concentrations of the alcohol/water mixtures in this aspect will determine the overall solvent profile across the zone. In one non-limiting example, the water:alcohol ratio of the eluent in each zone is the same, i.e., the same alcohol/water mixture is introduced to each zone.

Zones

In some aspects, the SMB apparatus used for separating at least one amine chosen from diamines and ω-aminoacids from a feed mixture may comprise only one separation zone or may comprise a plurality of separation zones.

In one exemplary aspect, when the desired amine(s) to be separated from the feed mixture elute faster than or elute slower than other components present in the feed mixture, the SMB may comprise only one zone.

In one exemplary aspect, two or more separation zones are used, for instance, 2 to 5 separation zones may be used. In some aspects, the components separated in each zone have different polarities. Each zone may contain one or more injection points for a feed mixture; one or more injection points for an eluent, the eluent comprising, for example, an aqueous alcohol; a take-off point for an extract stream; and a take-off point for a raffinate stream. In one aspect, part of the extract and/or raffinate streams recycled back into the same zone, and for example, the eluent and/or recycle stream may be adjusted such that the diamines and/or ω-aminoacids can be separated from different components of the feed mixture in each zone.

In some aspects where the SMB has two zones, the process for separating at least one amine chosen from diamines and ω-aminoacids from a feed mixture such as a fermentation product may comprise: introducing the feed mixture to a SMB chromatography apparatus having a first zone and a second zone, each of the first zone and the second zone comprising a plurality of linked chromatography columns, one or more eluent, an extract stream, and a raffinate stream collecting from the plurality of linked chromatography columns.

In certain aspects, the raffinate stream enriched with more polar components than the feed mixture and comprises the at least one amine is collected from the first zone and subsequently introduced to a nonadjacent column in the second zone. In one aspect, the at least one amine is separated from compounds having higher polarity than the at least one amine in the second zone.

In certain aspects, the raffinate stream enriched with less polar components than the feed mixture and comprises the at least one amine is collected from the first zone and subsequently introduced to a column, such as a nonadjacent column, in the second zone. In one aspect, the at least one amine is separated from compounds having lower polarity than the at least one amine in the second zone.

In certain aspects, the raffinate stream enriched with higher polar components than the feed mixture and comprises the at least one amine is collected from the second zone and subsequently introduced to a column, such as a nonadjacent column, in the first zone. In one aspect, the at least one amine is separated from compounds having higher polarity than the at least one amine in the first zone.

In certain aspects, the raffinate stream enriched with less polar components than the feed mixture and comprises the at least one amine is collected from the second zone and subsequently introduced to a column, such as a nonadjacent column, in the first zone. In one aspect, the at least one amine is separated from compounds having lower polarity than the at least one amine in the first zone.

In certain aspects, the extract stream enriched with more polar components than the feed mixture and comprises the at least one amine is collected from the first zone and subsequently introduced to a column, such as a nonadjacent column, in the second zone. In one aspect, the at least one amine is separated from compounds having higher polarity than the at least one amine in the second zone.

In certain aspects, the extract stream enriched with less polar components than the feed mixture and comprises the at least one amine is collected from the first zone and subsequently introduced to a column, such as a nonadjacent column, in the second zone. In one aspect, the at least one amine is separated from compounds having lower polarity than the at least one amine in the second zone.

In certain aspects, the extract stream enriched with higher polar components than the feed mixture and comprises the at least one amine is collected from the second zone and subsequently introduced to a column, such as a nonadjacent column, in the first zone. In one aspect, the at least one amine is separated from compounds having higher polarity than the at least one amine in the first zone.

In certain aspects, the extract stream enriched with less polar components than the feed mixture and comprises the at least one amine is collected from the second zone and subsequently introduced to a column, such as a nonadjacent column, in the first zone. In one aspect, the at least one amine is separated from compounds having lower polarity than the at least one amine in the first zone.

In some aspects where the SMB has two zones, the eluent in the first zone may contain more alcohol than the eluent in the second zone, and the second zone is downstream of the first zone with respect to the flow of eluent in the system. Thus, the eluent in the system typically may move from the first zone to the second zone. Conversely, the solid adsorbent phase typically moves from the second zone to the first zone. In one exemplary aspect, the two zones do not overlap, i.e. there are no chromatographic columns which are in both zones.

In some aspect, the SMB apparatus has a first zone, a second zone, and a third zone. In one non-limiting example where the eluent is aqueous alcohol, the water:alcohol ratios of the aqueous alcohol eluent present in the first, second, and third zones may be different. As will be evident to one skilled in the art, this has the consequence that impurities having different polarities can be removed in each zone.

In some aspects where the SMB has three zones, the eluent in the first zone can contain more alcohol than the eluent in the second zone and the third zone, and the first zone is upstream of the second and third zones with respect to the flow of eluent in the system. For example, the eluent in the second zone contains more alcohol than eluent in the third zone and the second zone is upstream of the third zone with respect to the flow of eluent in the system. Further as an example, in the first zone, the diamines and/or ω-aminoacids product is separated from components of the feed mixture which are less polar than the diamines and/or ω-aminoacids product. Also further as an example, in the second zone, the diamines and/or ω-aminoacids product is separated from components of the feed mixture which are less polar than the diamines and/or ω-aminoacids product but more polar than the components separated in the first zone. Further as an additional example, in the third zone, the diamines and/or ω-aminoacids product is separated from components of the feed mixture which are more polar than the at least one amine.

Columns

As noted above, SMB may comprise one or more separation zones, and in some aspects, each separation zone may comprise a plurality of linked chromatography columns.

According to certain aspects, the total number of columns present in SMB may range from 4 to 30 columns. For example, in one aspect, SMB apparatus may comprise 8 or more, for example 15 or more columns. Further as nonlimiting examples, SMB apparatus may comprise 15 or 16 columns, 19 or 20 columns, or 25 or 30 columns.

In some aspects, each zone may comprise approximately equal share of the total number of columns. For example, in the case of an apparatus configured with two zones, each zone may comprise approximately half of the total number of chromatographic columns in the system. The first zone can comprise 4 or more, for example 8 or more, or about 8 columns. The second zone can comprise 4 or more, for example 7 or more, or about 7 or 8 columns.

The dimensions of the columns used in the apparatus will depend on the volume of feed mixture to be purified. According to certain aspects, the diameter of each column can range between 10 mm and 5 m, for example between 5 mm and 500 mm, between 25 and 250 mm, between 50 and 100 mm, between 70 and 80 mm, between 0.5 m and 5 m, between 1 m and 4 m, or between 2 m and 5 m. According to certain aspects, the length (i.e., height) of each column can be between 10 cm and 5 m, for example between 10 and 200 cm, between 25 and 150 cm, between 70 and 110 cm, between 80 and 100 cm, between 0.5 m and 5 m, between 1 m and 4 m, between 2 m and 5 m, or between 3 m and 4 m.

The columns in each zone can have identical dimensions but may, for certain applications, have different dimensions.

Flow Rates

The flow rates to the column may be limited by maximum pressures across the series of columns and may depend on the column dimensions and particle size of the solid phases. Larger diameter columns may need higher flows to maintain linear flow through the columns.

In some aspects, for the typical column sizes outlined above, and for an apparatus having two zones, the flow rate of eluent into the first zone can be from 1 to 3,000 L/min, for example from 1 to 4.5 L/min, from 1.5 to 2.5 L/min, from 100 to 2,000 L/min, from 200 to 1,500 L/min, or from 200 to 1,200 L/min. The flow rate of the extract from the first zone can be from 0.1 to 1,000 L/min, for example from 0.1 to 2.5 L/min, from 0.5 to 2.25 L/min, from 100 to 1,000 L/min, from 200 to 1,000 L/min, from 100 to 400 L/min, or from 700 to 1,000 L/min. In one aspect where part of the extract from the first zone can be recycled back into the first zone, the flow rate of recycle can be for example from 0.7 to 600 L/min, from 100 to 700 L/min, from 250 to 600 L/min, from 0.7 to 1.4 L/min, for example about 1 L/min, about 375 L/min, about 80 L/min, or about 320 L/min. The flow rate of the raffinate from the first zone can be from 0.2 to 3,000 L/min, for example from 0.2 to 2.5 L/min, from 0.3 to 2.0 L/min, from 100 to 3,000 L/min, from 200 to 3,000 L/min, from 400 to 2,800 L/min, from 300 to 800 L/min, from 2,000 to 3,000 L/min. And in one aspect where part of the raffinate from the first zone can be recycled back into the first zone, the flow rate of recycle can be for example from 0.3 to 1,200 L/min, from 100 to 1,200 L/min, from 0.3 to 1.0 L/min, for example about 0.5 L/min, about 400 L/min, about 70 L/min, or about 350 L/min. In some aspects, the flow rate of introduction of a feed mixture such as a fermentation product into the first zone can be from 5 mL to 3,000 L/min, for example from 5 to 150 mL/min, from 10 to 100 mL/min, from 20 to 60 mL/min, from 100 to 3,000 L/min, from 200 to 2600 L/min, or from 400 to 2500 L/min.

In some aspects, for the typical column sizes outlined above, and for an apparatus having two zones, the flow rate of eluent into the second zone can be from 1 to 2,500 L/min, for example from 1 to 4 L/min, from 1.5 to 3.5 L/min, from 100 to 2,000 L/min, from 200 to 1,500 L/min, or from 200 to 1,200 L/min. The flow rate of the extract from the second zone can be from 0.5 to 900 L/min, for example from 0.7 to 1.9 L/min, from 120 to 900 L/min, from 200 to 800 L/min, from 100 to 400 L/min, or from 700 to 1,000 L/min. In one aspect where part of the extract from the second zone is recycled back into the second zone, the flow rate of recycle can be for example from 0.6 to 600 L/min, from 200 to 600 L/min, from 0.6 to 1.4 L/min, for example from 0.7 to 1.1 L/min, about 0.9 L/min, about 340 L/min, about 70 L/min, or about 290 L/min. The flow rate of the raffinate from the second zone can be from 0.5 to 3,000 L/min, for example from from 0.5 to 2.5 L/min, 0.7 to 1.8 L/min, about 1.4 L/min, from 100 to 3,000 L/min, from 200 to 3,000 L/min, from 400 to 2,800 L/min, from 300 to 800 L/min, from 2,000 to 3,000 L/min.

In some aspects, part of one or more of the extract stream from the first zone, the raffinate stream from the first zone, the extract stream from the second zone, and the raffinate stream from the second zone can be recycled back into the same zone, for example into an adjacent column in the same zone.

This recycle is different from the feeding of an extract or raffinate stream into a non-adjacent column in another zone. Rather, the recycle involves feeding part of the extract or raffinate stream out of a zone back into the same zone, for example into an adjacent column in the same zone.

Figure 9:
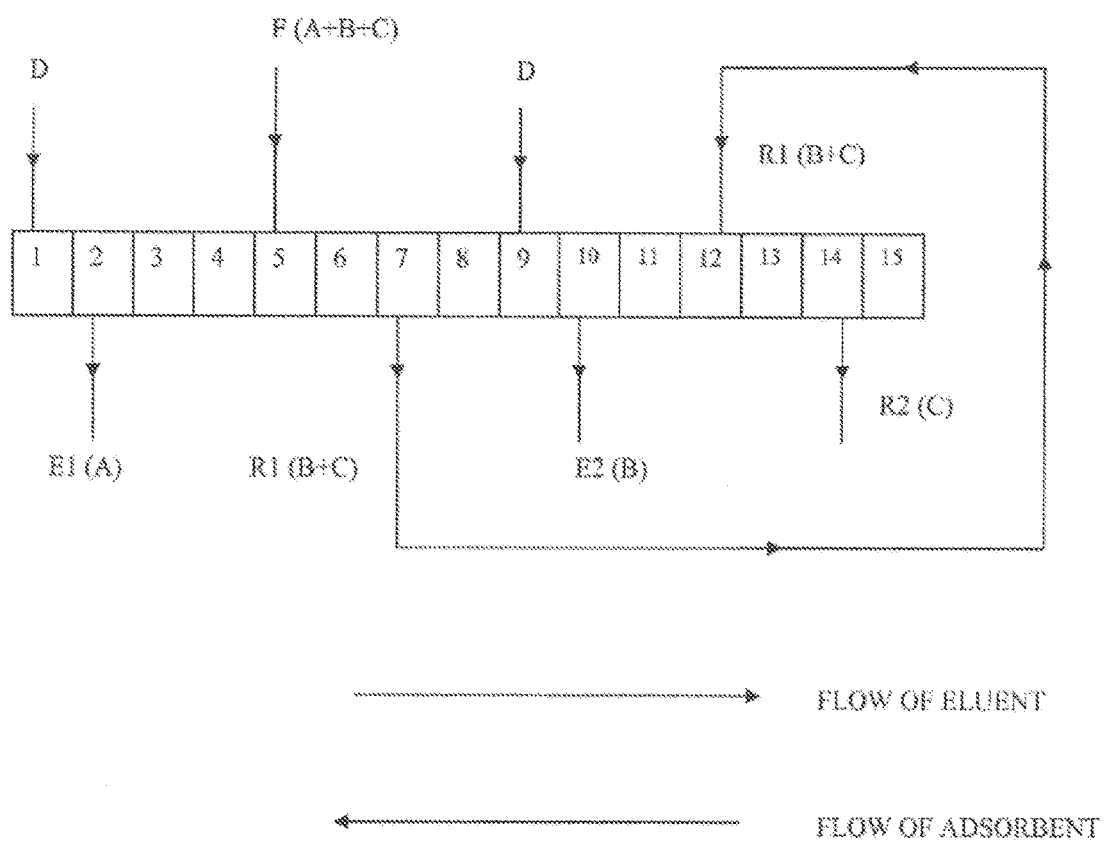
FIG. 9 illustrates an exemplary aspect for separating desired diamine(s) and/or a ω-aminoacid(s) from faster and slower running components (i.e. more polar and less polar impurities).
Figure 10:
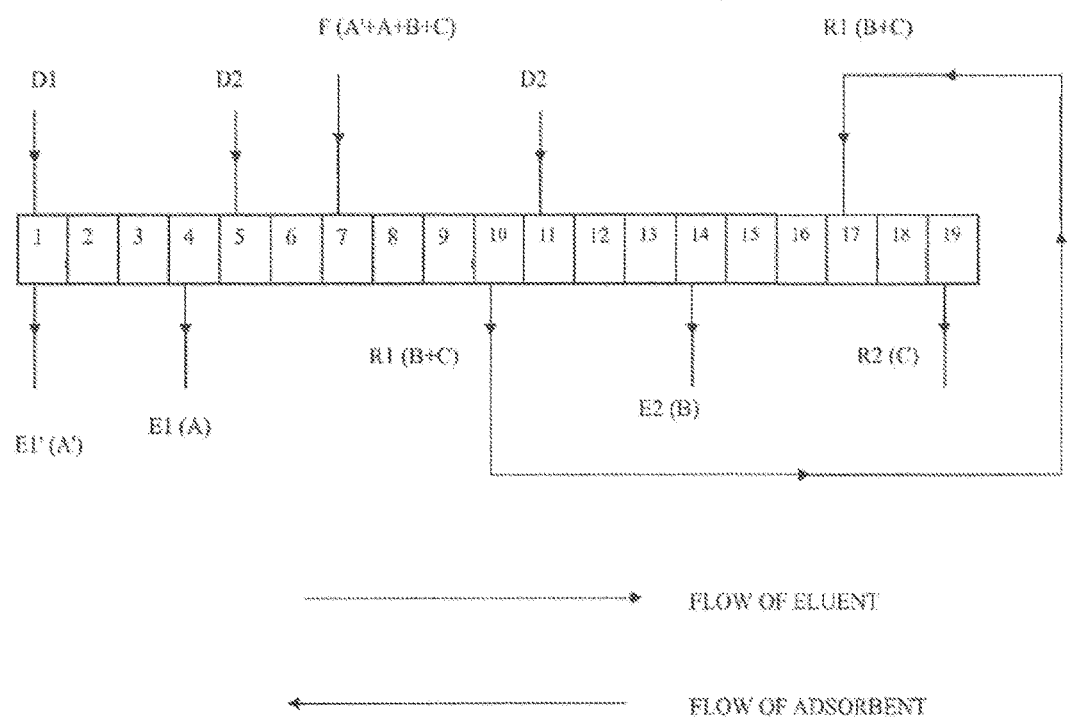
FIG. 10 illustrates an exemplary aspect for separating desired diamine(s) and/or ω-aminoacid(s) from faster and slower running components (i.e. more polar and less polar impurities).

In one aspect, the rate at which liquid collected via the extract or raffinate stream from the first or second zones is recycled back into the same zone can be the rate at which liquid collected via that stream is fed back into the same zone, for example into an adjacent column in the same zone. This can be seen with reference to FIG. 9. The rate of recycle of extract in the first zone is the rate at which extract collected from the bottom of column 2 is fed into the top of column 3, i.e. the flow rate of liquid into the top of column 3. The rate of recycle of extract in the second zone is the rate at which extract collected at the bottom of column 10 is fed into the top of column 11, i.e. the flow rate of liquid into the top of column 11.

In one aspect, recycle of the extract and/or raffinate streams can be effected by feeding the liquid collected via that stream into a container, and then pumping an amount of that liquid from the container back into the same zone. In this case, the rate of recycle of liquid collected via a particular extract or raffinate stream, for example back into an adjacent column in the same zone, is the rate at which liquid is pumped out of the container back into the same zone, for example into an adjacent column.

In one aspect, the amount of liquid being introduced into a zone via the eluent and feed streams is balanced with the amount of liquid removed from a zone, and recycled back into the same zone. Thus, with reference to FIG. 9, for the extract stream, the flow rate of eluent (desorbent) into the first or second zone (D) is equal to the rate at which liquid collected via the extract stream from that zone accumulates in a container (E1/E2) added to the rate at which extract is recycled back into the same zone (D-E1/D-E2). For the raffinate stream in a zone, the rate at which extract is recycled back into a zone (D-E1/D-E2) added to the rate at which feed is introduced into a zone (F/R1) is equal to the rate at which liquid collected via the raffinate stream from that zone accumulates in a container (R1/R2) added to the rate at which raffinate is recycled back into the same zone (D+F−E1−R1/D+R1−E2−R2).

In one aspect, the rate at which liquid collected from a particular extract or raffinate stream from a zone accumulates in a container can also be thought of as the net rate of removal of that extract or raffinate stream from that zone.

In one aspect, the rate at which liquid collected via the extract stream out of the first zone is recycled back into the first zone can differ from the rate at which liquid collected via the extract stream out of the second zone is recycled back into the second zone, and/or the rate at which liquid collected via the raffinate stream out of the first zone is recycled back into the first zone can differ from the rate at which liquid collected via the raffinate stream out of the second zone is recycled back into the second zone.

In some aspects, varying the rate at which liquid collected via the extract and/or raffinate streams in each zone is recycled back into the same zone has the effect of varying the amount of more polar and less polar components present in the other extract and raffinate streams. Thus, for example, a lower extract recycle rate results in fewer of the less polar components in that zone being carried through to the raffinate stream in that zone. A higher extract recycle rate results in more of the less polar components in that zone being carried through to the raffinate stream in that zone. This can be seen, for example, in the specific aspect of the invention shown in FIG. 6. The rate at which liquid collected via the extract stream in the first zone is recycled back into the same zone (D-E1) will affect to what extent any of component A is carried through to the raffinate stream in the first zone (R1).

In one aspect, the rate at which liquid collected via the extract stream from the first zone is recycled back into the first zone can be faster than the rate at which liquid collected via the extract stream from the second zone is recycled back into the second zone. As an example, a raffinate stream containing the diamines and/or ω-aminoacids product together with more polar components is collected from a column in the first zone and introduced to a nonadjacent column in the second zone, and the rate at which liquid collected via the extract stream from the first zone is recycled back into the first zone can be faster than the rate at which liquid collected via the extract stream from the second zone is recycled back into the second zone.

Further as an example, the rate at which liquid collected via the extract stream from the first zone is recycled back into the first zone can be slower than the rate at which liquid collected via the extract stream from the second zone is recycled back into the second zone.

In one aspect, the rate at which liquid collected via the raffinate stream from the second zone is recycled back into the second zone can be faster than the rate at which liquid collected via the raffinate stream from the first zone is recycled back into the first zone. For example, an extract stream containing the diamines and/or ω-aminoacids product together with less polar components can be collected from a column in the second zone and introduced to a nonadjacent column in the first zone, and the rate at which liquid collected via the raffinate stream from the second zone is recycled back into the second zone can be faster than the rate at which liquid collected via the raffinate stream from the first zone is recycled back into the first zone.

Further as an example, the rate at which liquid collected via the raffinate stream from the second zone is recycled back into the second zone can be slower than the rate at which liquid collected via the raffinate stream from the first zone is recycled back into the first zone.

In some aspects, the step time, i.e. the time between shifting the points of injection of the feed mixture and eluent, and the various take off points of the collected fractions depends on the number and dimensions of the columns used, and the flow rate through the apparatus. For example, the step time can be from 100 to 1200 seconds, such as from 100 to 1000 seconds, from 200 to 800 seconds, or from about 250 to about 750 seconds. Further as an example, the step time can be from 100 to 400 seconds, or from 200 to 300 seconds, or about 250 seconds. Also further as an example, the step time can be from 600 to 900 seconds, or from 700 to 800 seconds, or about 750 seconds. In other aspects, the step time can be from 400 to about 800 seconds, from about 500 to 700 seconds, or about 600 seconds.

The process for separating at least one amine chosen from diamines and ω-aminoacids from a feed mixture such as a fermentation product may be operated over a broad range of temperatures and pressure. In some aspects, the process can be conducted at from 15 to 65° C., for example at from 20 to 65° C., such as at 60° C. or from 30 to 55° C. In one aspect, the process can be carried out at room temperature or at elevated temperatures. Pressure may not be a critical feature of the process. Thus, with the above ranges of temperature, pressures between about 330 to about 3500 kPa gauge may be used. Typically, the pressure range is between about 350 and 2000 kPa gauge.

In some aspects, for process for separating at least one amine chosen from diamines and ω-aminoacids from a feed mixture may comprise: introducing a feed mixture into one zone (for example the first zone) of a SMB, collecting a first intermediate stream enriched with the diamines and/or ω-aminoacids product and introducing the first intermediate stream into another zone (for example the second zone) of the SMB. Thus, in one aspect where the SMB system has two zones, the method involves either (a) collecting a first intermediate stream from the first zone and introducing it into the second zone, or (b) collecting a first intermediate stream from the second zone and introducing it into the first zone. In this way, the diamines and/or ω-aminoacids product can be separated from both more and less polar components in a single method.

In one aspect, either (a) a raffinate stream containing the diamines and/or ω-aminoacids product together with more polar components can be collected from a column in the first zone and introduced to a nonadjacent column in the second zone, or (b) an extract stream containing the diamines and/or ω-aminoacids product together with less polar components can be collected from a column in the second zone and introduced to a nonadjacent column in the first zone.

In some aspects, the SMB apparatus has two zones, and the method for separating at least one amine chosen from diamines and ω-aminoacids from a feed mixture may comprise: (i) introducing the feed mixture into the first zone of the SMB, and removing a first raffinate stream enriched with the diamines and/or ω-aminoacids product and a first extract stream depleted of the diamines and/or ω-aminoacids product, and (ii) introducing the first raffinate stream into the second zone, removing a second raffinate stream depleted of the diamines and/or ω-aminoacids product, and collecting a second extract stream to obtain the diamines and/or ω-aminoacids product.

Figure 2:
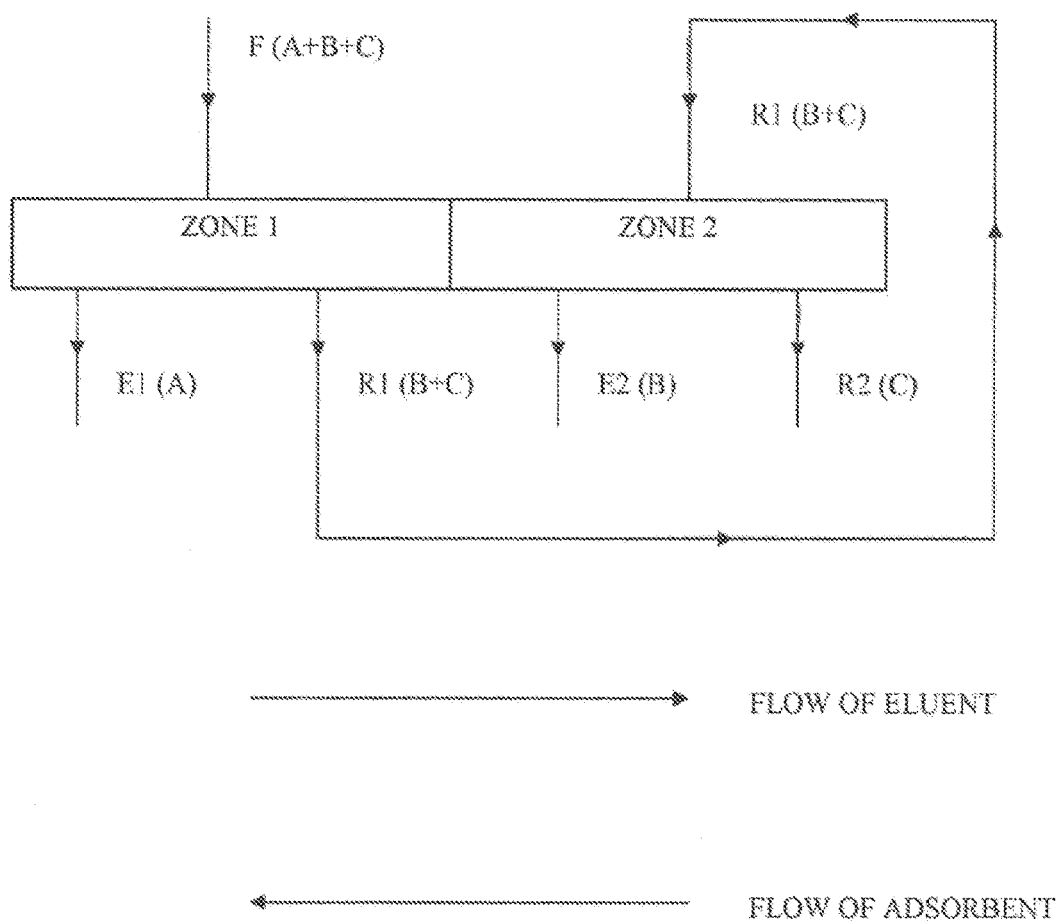
FIG. 2 illustrates an exemplary aspect for separating desired diamine(s) and/or ω-aminoacid(s) from faster and slower running components (i.e. more polar and less polar impurities).

The aspects described immediately above are further illustrated in FIG. 2. A feed mixture F comprising the diamines and/or ω-aminoacids product (B) and more polar (C) and less polar (A) components is introduced into the first zone. In the first zone, the less polar components (A) are removed as extract stream E1. The diamines and/or ω-aminoacids product (B) and more polar components (C) are removed as raffinate stream R1. Raffinate stream R1 is then introduced into the second zone. In the second zone, the more polar components (C) are removed as raffinate stream R2. The diamines and/or ω-aminoacids product (B) is collected as extract stream E2.

The aspects described above are illustrated in more detail in FIG. 4, which is identical to FIG. 2 except that the points of introduction of the alcohol desorbent (D) and water (W) into each zone are shown. The alcohol desorbent (D) and water (W) together make up the eluent. The (D) phase can be essentially pure alcohol, but may, in certain aspects be an alcohol/water mixture comprising mainly alcohol. The (W) phase can be essentially pure water, but may, in certain aspects be an alcohol/water mixture comprising mainly water, for example a 98% water/2% methanol mixture.

Figure 6:
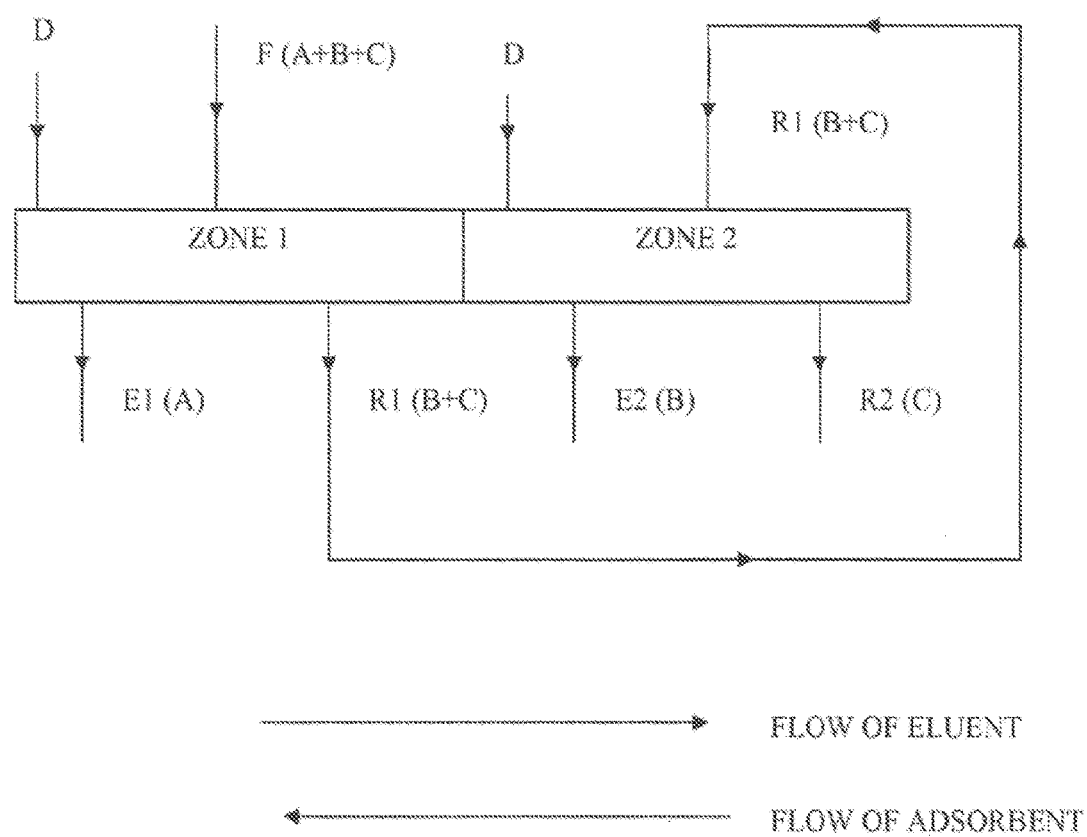
FIG. 6 illustrates an exemplary aspect for separating desired diamine(s) and/or ω-aminoacid(s) from faster and slower running components (i.e. more polar and less polar impurities).

A further illustration of these aspects is shown in FIG. 6. Here there is no separate water injection point, and instead an aqueous alcohol desorbent is injected at (D).

Figure 4:
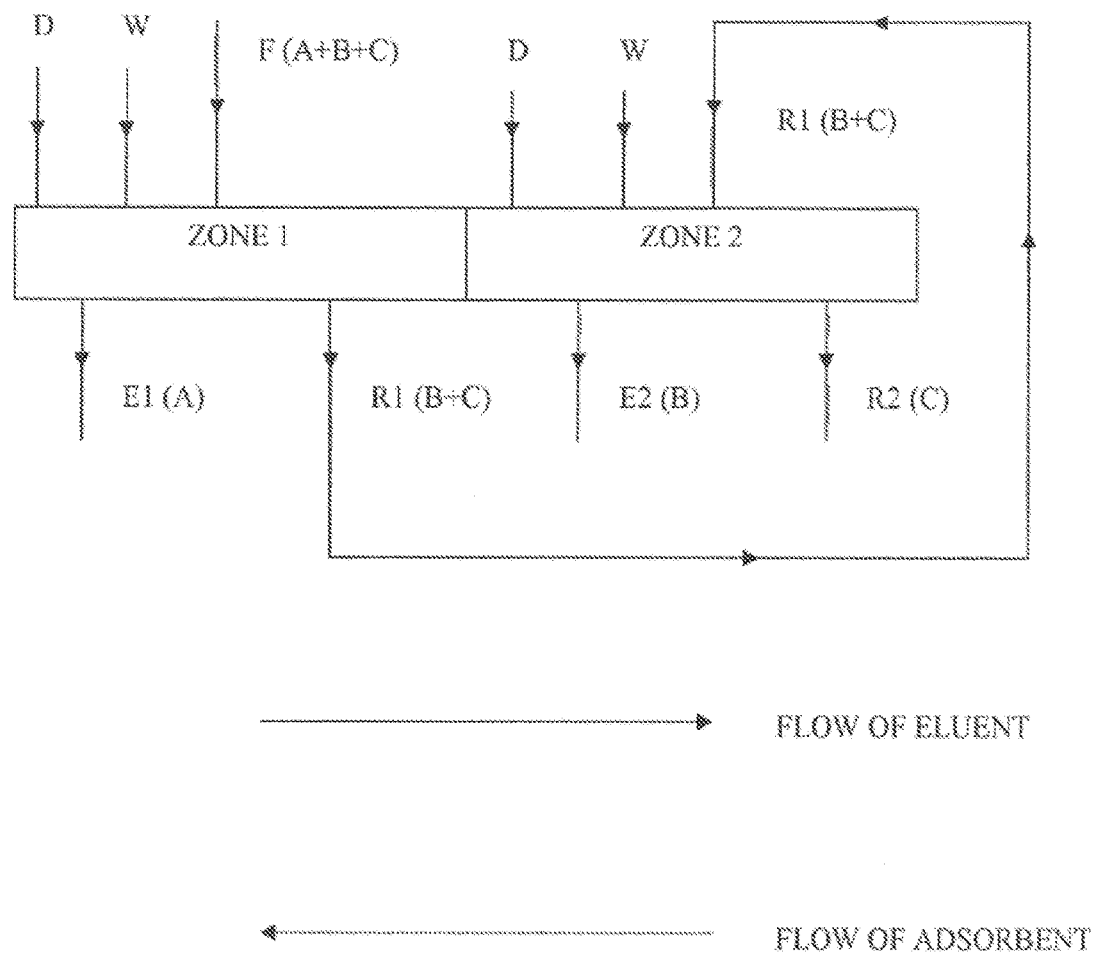
FIG. 4 illustrates an exemplary aspect for separating desired diamine(s) and/or ω-aminoacid(s) from faster and slower running components (i.e. more polar and less polar impurities).

The separation into raffinate and extract stream can be aided by varying the desorbing power of the eluent within each zone. This can be achieved by introducing the alcohol (or alcohol rich) component of the eluent and the water (or water rich) component at different points in each zone. Thus, as an example, the alcohol is introduced upstream of the extract take-off point and the water is introduced between the extract take-off point and the point of introduction of the feed into the zone, relative to the flow of eluent in the system. This is shown in FIG. 4.

Alternatively, the separation can be aided by varying the rates at which liquid collected via the extract and raffinate streams from the two zones is recycled back into the same zone.

For example, the rate at which liquid collected via the extract stream from the first zone is recycled back into the first zone may be faster than the rate at which liquid collected via the extract stream from the second zone is recycled back into the second zone; or the water:alcohol ratio of the eluent in the first zone may be lower than that in the second zone.

In one aspect, the first raffinate stream in the first zone can be removed downstream of the point of introduction of the feed mixture into the first zone, with respect to the flow of eluent in the first zone.

In one aspect, the first extract stream in the first zone can be removed upstream of the point of introduction of the feed mixture into the first zone, with respect to the flow of eluent in the first zone.

In one aspect, the second raffinate stream in the second zone can be removed downstream of the point of introduction of the first raffinate stream into the second zone, with respect to the flow of eluent in the second zone.

In one aspect, the second extract stream in the second zone can be collected upstream of the point of introduction of the first raffinate stream into the second zone, with respect to the flow of eluent in the second zone.

In one aspect, the alcohol or aqueous alcohol can be introduced into the first zone upstream of the point of removal of the first extract stream, with respect to the flow of eluent in the first zone.

In one aspect where water is introduced into the first zone, the water can be introduced into the first zone upstream of the point of introduction of the feed mixture but downstream of the point of removal of the first extract stream, with respect to the flow of eluent in the first zone.

In one aspect, the alcohol or aqueous alcohol can be introduced into the second zone upstream of the point of removal of the second extract stream, with respect to the flow of eluent in the second zone.

In one aspect, when water is introduced into the second zone, the water can be introduced into the second zone upstream of the point of introduction of the first raffinate stream but downstream of the point of removal of the second extract stream, with respect to the flow of eluent in the second zone.

In some aspects, the SMB apparatus has two zones, and the method for separating at least one amine chosen from diamines and ω-aminoacids from a feed mixture may comprise: (i) introducing the feed mixture into the second zone, and removing a first raffinate stream depleted of the diamines and/or ω-aminoacids product and a first extract stream enriched in the diamines and/or ω-aminoacids product, and (ii) introducing the first extract stream into the first zone, removing a second extract stream depleted of the diamines and/or ω-aminoacids product, and collecting a second raffinate stream to obtain the diamines and/or ω-aminoacids product.

Figure 3:
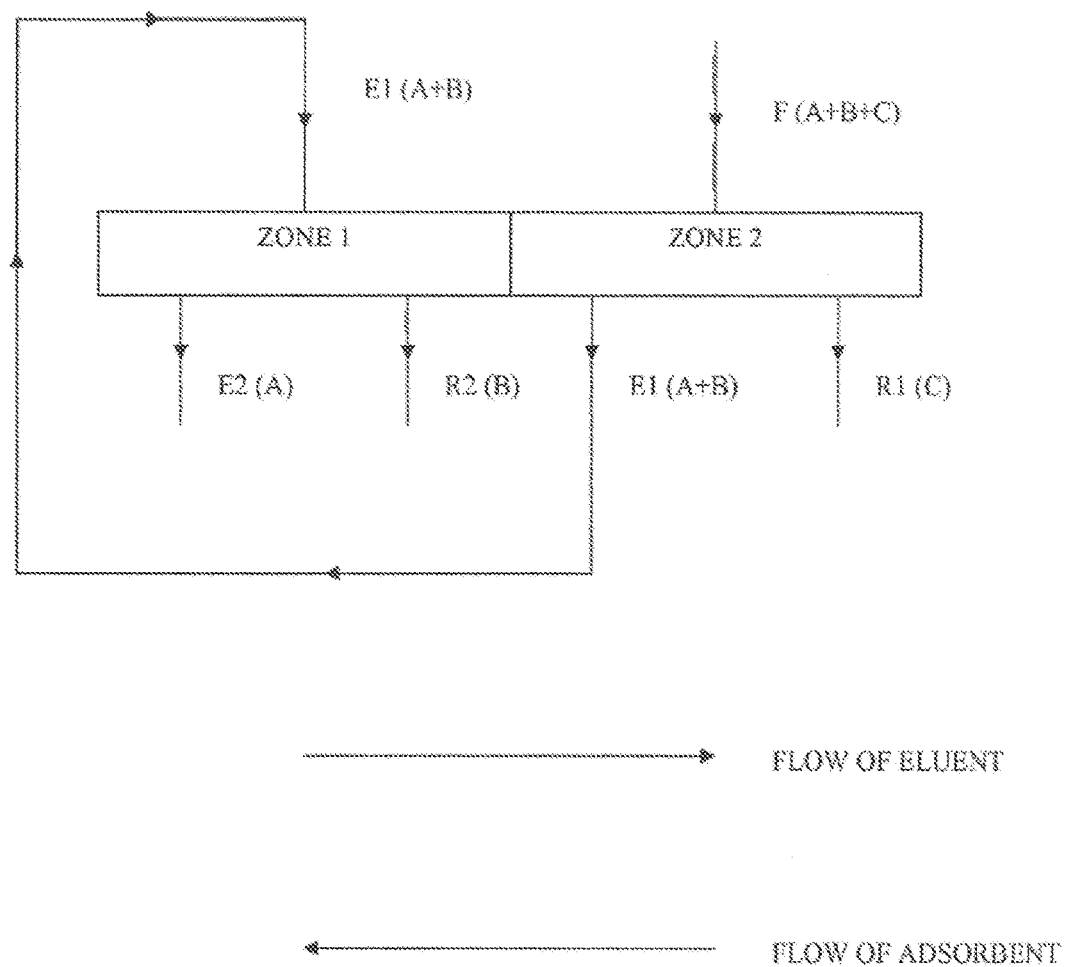
FIG. 3 illustrates an exemplary aspect for separating desired diamine(s) and/or ω-aminoacid(s) from faster and slower running components (i.e. more polar and less polar impurities).

The aspects described immediately above are illustrated in FIG. 3. A feed mixture F comprising the diamines and/or ω-aminoacids product (B) and more polar (C) and less polar (A) components is introduced into the second zone. In the second zone, the more polar components (C) are removed as raffinate stream R1. The diamines and/or ω-aminoacids product (B) and less polar components (A) are collected as extract stream E1. Extract stream E1 is then introduced to the first zone. In the first zone, the less polar components (A) are removed as extract stream E2. The diamines and/or ω-aminoacids product (B) is collected as raffinate stream R2.

Figure 5:
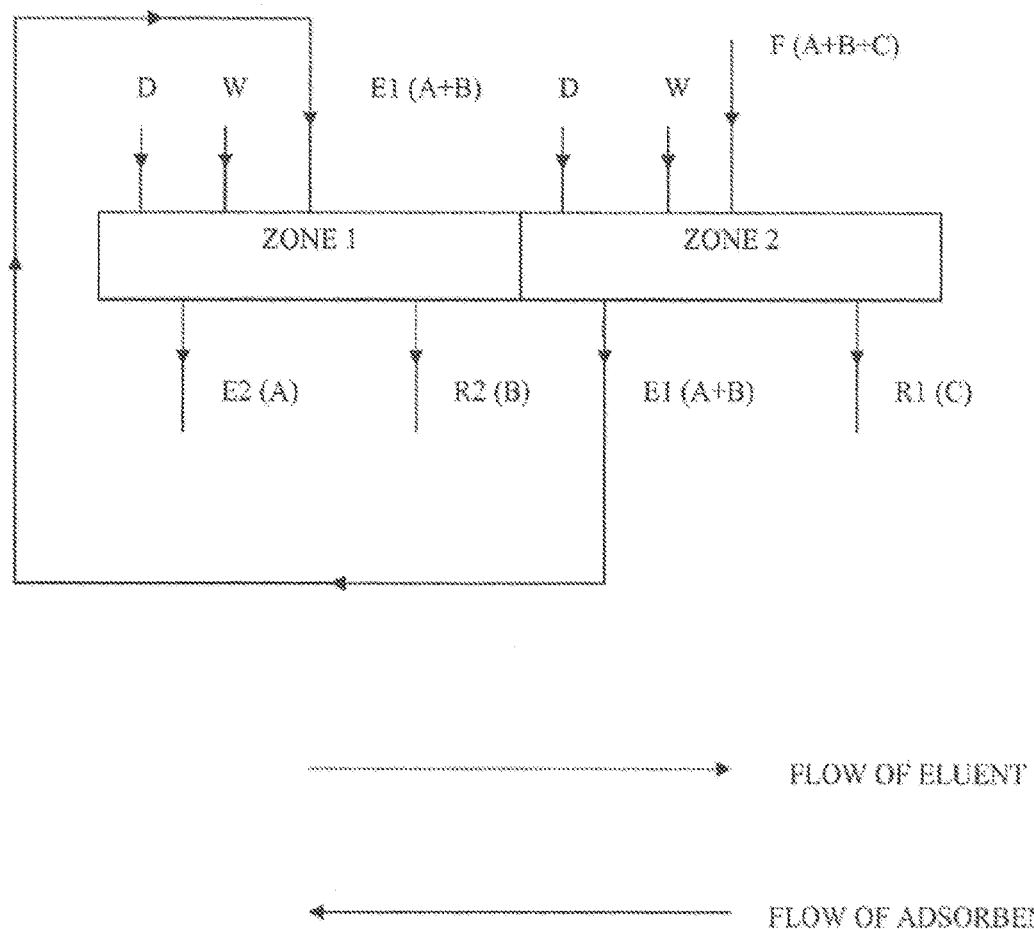
FIG. 5 illustrates an exemplary aspect for separating desired diamine(s) and/or ω-aminoacid(s) from faster and slower running components (i.e. more polar and less polar impurities).

These aspects are further illustrated in more detail in FIG. 5, which is identical to FIG. 3 except that the points of introduction of the short chain alcohol desorbent (D) and water (W) into each zone are shown. As above, the (D) phase can be essentially pure alcohol, but may, in certain aspects be an alcohol/water mixture comprising mainly alcohol. The (W) phase can be essentially pure water, but may, in certain aspects be an alcohol/water mixture comprising mainly water, for example a 98% water/2% methanol mixture.

Figure 7:
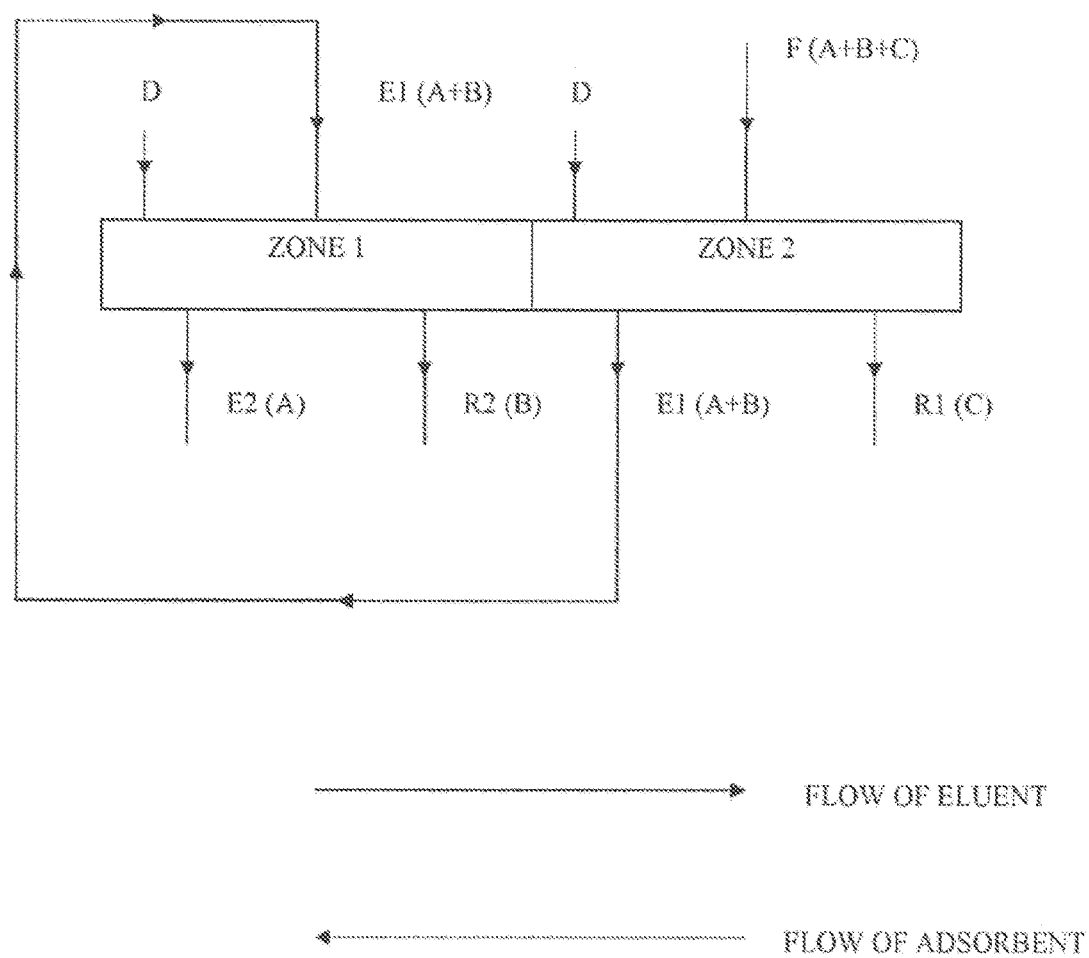
FIG. 7 illustrates an exemplary aspect for separating desired diamine(s) and/or ω-aminoacid(s) from faster and slower running components (i.e. more polar and less polar impurities).
Figure 8:
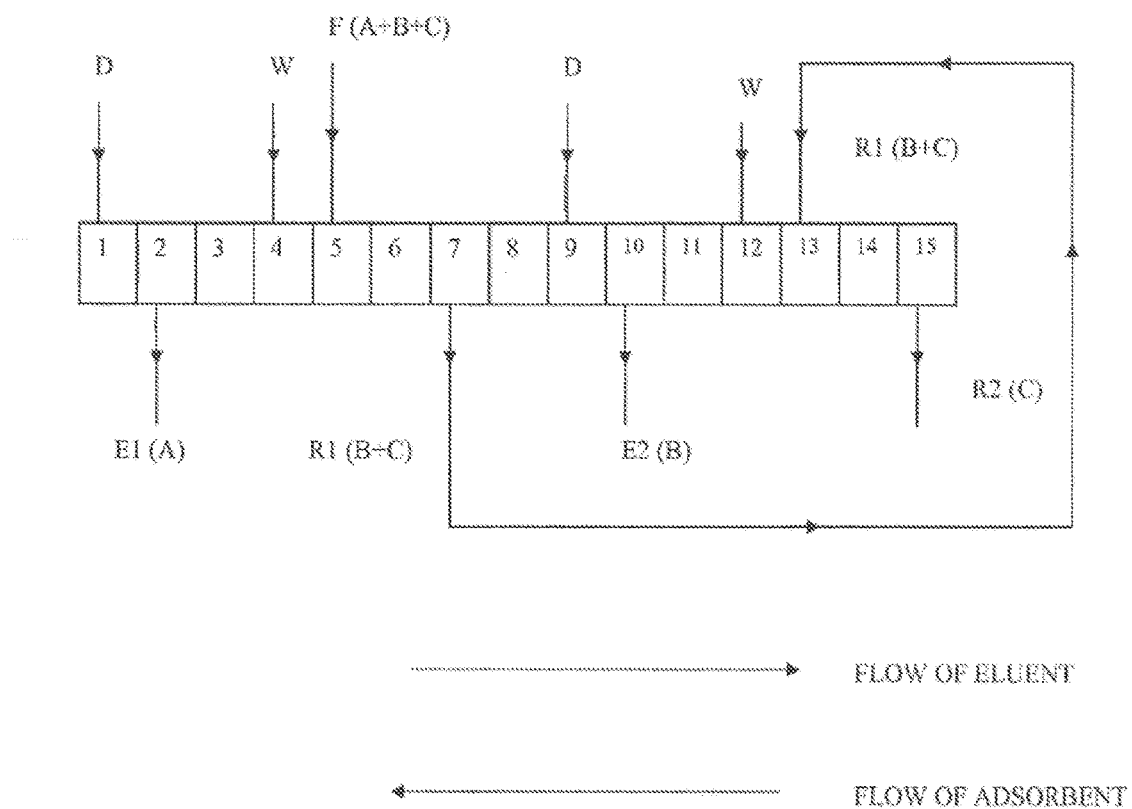
FIG. 8 illustrates an exemplary aspect for separating desired diamine(s) and/or ω-aminoacid(s) from faster and slower running components (i.e. more polar and less polar impurities).

A further illustration of these aspects is shown in FIG. 7. Here there is no separate water injection point, and instead an aqueous alcohol desorbent is injected at (D).

In one aspect, the rate at which liquid collected via the raffinate stream from the second zone is reintroduced into the second zone can be faster than the rate at which liquid collected via the raffinate stream from the first zone is reintroduced into the first zone; or the water:alcohol ratio of the eluent in the first zone can be lower than that in the second zone.

In one aspect, the first raffinate stream in the second zone can be removed downstream of the point of introduction of the feed mixture into the second zone, with respect to the flow of eluent in the second zone.

In one aspect, the first extract stream in the second zone can be collected upstream of the point of introduction of the feed mixture into the second zone, with respect to the flow of eluent in the second zone.

In one aspect, the second raffinate stream in the first zone can be collected downstream of the point of introduction of the first extract stream into the first zone, with respect to the flow of eluent in the first zone.

In one aspect, the second extract stream in the first zone can be removed upstream of the point of introduction of the first extract stream into the first zone, with respect to the flow of eluent in the first zone.

In one aspect, the alcohol or aqueous alcohol can be introduced into the second zone upstream of the point of removal of the first extract stream, with respect to the flow of eluent in the second zone.

In one aspect where water is introduced into the second zone, the water can be introduced into the second zone upstream of the point of introduction of the feed mixture but downstream of the point of removal of the first extract stream, with respect to the flow of eluent in the second zone.

In one aspect, the alcohol or aqueous alcohol can be introduced into the first zone upstream of the point of removal of the second extract stream, with respect to the flow of eluent in the first zone.

In one aspect where water is introduced into the first zone, the water can be introduced into the first zone upstream of the point of introduction of the first raffinate stream but downstream of the point of removal of the second extract stream, with respect to the flow of eluent in the first zone.

In some aspects, the SMB apparatus may comprise a total of fifteen chromatographic columns. These are referred to as columns 1 to 15. The fifteen columns are arranged in series so that the bottom of column 1 is linked to the top of column 2, the bottom of column 2 is linked to the top of column 3 etc. This can optionally be via a holding container, with a recycle stream into the next column. The flow of eluent through the system is from column 1 to column 2 to column 3 etc. The flow of adsorbent through the system is from column 15 to column 14 to column 13 etc.

In one exemplary aspect, the SMB apparatus may comprise a total of fifteen chromatographic columns in two zones: the first zone may consist of eight adjacent columns, columns 1 to 8, which are connected as discussed above; the second zone may consist of seven columns, columns 9 to 15, which are connected as discussed above. Additionally, the bottom of column 8 in the first zone is linked to the top of column 9 in the second zone.

In some aspects, recovery of diamine or ω-aminoacid of interest (i.e., the portion that ends up in the SMB "product" stream) could range from 80 to 99% of the amount of diamine or ω-aminoacid of interest in the SMB feed. In some aspects, after SMB separation, the purity of diamine and/or ω-aminoacid of interest, on an organics-only basis (i.e., excluding desorbent and/or water), may range from about 85 to 99 wt %.

In some aspects, the diamine(s) and/or ω-aminoacid(s) recovered from SMB apparatus may be subject to one or more purification steps to further purify the the target α,ω-diamine or ω-aminoacid and produce a purified product stream containing the target α,ω-diamine or ω-aminoacid. The one or more purification steps may be chosen from, as non-limiting examples, evaporation, distillation, vacuum distillation, filtration, membrane separation, crystallization, evaporative crystallization, and cooling crystallization.

In a another aspect, when one or more components exhibit a much stronger affinity for the stationary phase adsorbent (i.e., much slower running components) than the other components, the feed mixture comprising at least one amine may be first introduced into a pre-treatment guard bed containing the stationary phase adsorbent to capture the much slower running components, forming a guard bed effluent of treated feed that is reduced in the much slower running components. The treated feed mixture is subsequently introduced into a SMB unit to separate the the at least one amine from the other remaining components. In another aspect, two parallel guard beds are employed, where one guard bed is operating to adsorb the much slower running components in the feed and produce a treated feed, while the other guard bed does not receive a feed and is instead being regenerated by introducing a desorbent to desorb the much slower running components from the stationary phase.

In another aspect, the guard bed can be extracted with a solvent to remove the slower running components. If the slower running components such as other unwanted diamines and/or ω-aminoacids, hydroxylated fatty acids, fatty acids, fatty acid esters, hydrocarbons, diacids, ω-hydroxyamines, or hydroxycarboxylic acids are unreacted starting material or intermediates in the chemical or biological preparation of diamines and ω-aminoacids, the recovered slower running components, after removal of unwanted solvents, may be recycled back to the chemical or biological processes.

In another aspect, the extract is fed to an extract desorbent recovery step to recover desorbent and produce a treated extract that is reduced in desorbent. The specific type of separation step will depend on the physical properties of the desorbent and other components in the extract. The extract desorbent recovery step can be selection from the non-limiting group comprising evaporation, distillation, crystallization, vacuum crystallization, and cooling crystallization. In one aspect, the desorbent that is recovered from the extract desorbent recovery step is recycled to the SMB unit. In another aspect, the components in the extract such as unwanted diamines and/or ω-aminoacids, hydroxylated fatty acids, fatty acids, fatty acid esters, hydrocarbons, diacids, ω-hydroxyamines, or hydroxycarboxylic acids are unreacted starting material or intermediates in the preparation of diacids may be recycled back to the chemical or biological processes.

In another aspect, the raffinate is fed to a raffinate desorbent recovery step to recover desorbent and produce a treated raffinate that is reduced in desorbent. The specific type of separation step will depend on the physical properties of the desorbent and other components in the raffinate. The raffinate desorbent recovery step may comprise one for more separation unit operations selected from the non-limiting group comprising evaporation, distillation, vacuum distillation, filtration, membrane separation, crystallization, evaporative crystallization, and cooling crystallization. In one aspect, the desorbent that is recovered from the raffinate desorbent recovery step is recycled to the SMB unit.

In another aspect, the raffinate is fed to a water removal step to produce treated raffinate that is reduced in water. The specific type of water removal step will depend on the nature of the components in the raffinate. The water removal step may comprise one or more separation unit operations selected from the non-limiting group comprising evaporation, distillation, vacuum distillation, filtration, membrane separation, crystallization, evaporative crystallization, and cooling crystallization. In one aspect the water that is recovered from the water removal step is recycled to the SMB unit. In one aspect the water that is recovered from the water removal step is recycled to a fermentation step.

EXAMPLES

Example 1

An aqueous feed mixture comprising 10 wt % hexamethylendiamine (HMD), 0.5 wt % 6-hydroxyaminohexane (6-HAH), and 0.5 wt % 6-aminocaproic acid (6-ACA) is fed at a flow rate of 146,199 kg/hr to a SMB unit comprising 15 columns. Each column contains an adsorbent bed 4 m in diameter by 4 m in height of Orpheus silica-based stationary phase adsorbent manufactured by Orochem Technologies Inc., Naperville, Ill., USA. The adsorbent is chosen such that 6-HAH and 6-ACA have a stronger affinity for the adsorbent than does HMD, thereby enabling recovering of a majority of the 6-HAH and 6-ACA in the extract, and a recovery of a majority of the HMD in the raffinate. A methanol desorbent (mobile phase) is fed to the SMB unit at a flow rate of 52,266 kg/hr. An extract is withdrawn from the SMB unit at a flow rate of 41,122 kg/hr. A raffinate is withdrawn from the SMB unit at a flow rate of 157,342 kg/hr.

At a time t, the aqueous feed mixture is fed to column 10, the methanol desorbent is fed to column 1, the extract is withdrawn from column 6, and the raffinate is withdrawn from column 14. Periodically, according to a step time, dt, the inlet and outlet flows are each shifted to the next higher numbered column (i.e., in the direction of liquid flow), simulating an opposite movement of each stationary phase adsorbent bed to the next lower numbered column. Any inlet or outlet flow that was previously directed to or from column 15 moves to or from column 1. In other words, at time t+dt, the aqueous feed mixture is fed to column 11, the methanol desorbent is fed to column 2, the extract is withdrawn from column 7, and the raffinate is withdrawn from column 15. The total cycle time for the 15-column SMB unit is 15×dt.

The step time, dt, is adjusted so that, at steady state, the composition of the extract is 1.7 wt % 6-ACA, 1.5 wt % 6-HAH, 1.7 wt % HMD, 3.2 wt % water, and the remainder methanol; the composition of the raffinate is 0.02 wt % 6-ACA, 0.07 wt % 6-AHA, 8.83 wt % HMD, 8.47 wt % methanol, and the remainder water; the HMD recovery in the raffinate is 95% and HMD purity in the raffinate is 99.0 wt % (on an solvent-free basis, i.e., excluding methanol and water).

What is claimed is:
1. A process for separating at least one amine from a feed mixture comprising:
    introducing a feed mixture comprising at least one amine chosen from diamines and ω-aminoacids into a simulated moving bed apparatus comprising a non-ionic resin to separate the at least one amine; and
    recovering a composition comprising the at least one amine with a purity higher than that in the feed mixture from the simulated moving bed apparatus.

2. The process according to claim 1 further comprising:
    subjecting the feed mixture to at least one solid-liquid separation prior to introducing the feed mixture into the simulated moving bed apparatus.
3. The process according to claim 2, wherein the at least one solid-liquid separation is chosen from cross-flow filtration, centrifugation, and dead-end filtration.
4. The process according to claim 1, wherein the feed mixture comprises a fermentation product.
5. The process according to claim 4, wherein the fermentation product is produced by at least one organism chosen from *Escherichia coli, Clostridium ljungdahlii, Clostridium autoethanogenurn, Clostridium kluyveri, Corynebacterium glutamicum,Cupriavidus* necator, *Cupriavidus metallidurans, Pseudomonas fluorescens, Pseudomonas putida, Pseudomonas oleavorans, Delftia acidovorans, Bacillus subtillis, Lactobacillus delbrueckii, Lactococcus lactis, Rhodococcus equi, Aspergillus niger, Saccharomyces cerevisiae, Pichia pastoris, Yarrowia lipolytica, Issathenkia orientalis, Debaryomyces hansenii, Arxula adenoinivorans,* and *Kluyveromyces lactis.*
6. The process according to claim 1, wherein the simulated moving bed apparatus comprises only one zone.
7. The process according to claim 1, wherein the simulated moving bed apparatus comprises more than one zone.
8. The process according to claim 7, further comprising
    collecting from a column in a zone a raffinate stream comprising the at least one amine, wherein a ratio of less polar to more polar components in the raffinate stream is increased or decreased relative to the feed mixture,
    introducing the raffinate stream into another zone; and
    recovering the at least one amine from said another zone.
9. The process according to claim 7, wherein
    collecting from a column in a zone an extract stream comprising the at least one amine, wherein a ratio of less polar to more polar components in the extract stream is increased or decreased relative to the feed mixture,
    introducing the extract stream into another zone; and
    recovering the at least one amine from said another zone.
10. The process according to claim 8, wherein the raffinate stream is introduced into a column nonadjacent to the column from which the raffinate is collected.
11. The process according to claim 9, wherein the extract stream is introduced into a column nonadjacent to the column from which the extract is collected.
12. The process according to claim 7, wherein part of an extract stream and/or a raffinate stream from one zone is/are recycled back into the same or different zone.
13. The process according to claim 1, wherein the simulated moving bed apparatus further comprises one or more eluents comprising at least one solvent chosen from water and alcohol.
14. The process according to claim 1, wherein the feed mixture comprises at least one diamine chosen from pentamethylenediamine, hexamethylenediamine, heptamethylenediamine, and 1,12-diaminododecane.
15. The process according to claim 1, wherein the feed mixture comprises at least one ω-aminoacid chosen from 5-aminopentaoic acid, 6-aminocaporic acid, 7-aminoheptanoic acid, 11-aminounidecanoic acid, and 12-aminolauric acid.
16. The process according to claim 1 further comprising:
    subjecting the composition recovered from the simulated moving bed apparatus to at least one separation step.
17. The process according to claim 16, wherein the at least one separation step is chosen from evaporation, distillation, vacuum distillation, filtration, membrane separation, crystallization, evaporative crystallization, and cooling crystallization.

18. The process according to claim 1, wherein the simulated moving bed apparatus comprises at least 4 columns.

19. The process according to claim 1, further comprising:
introducing the feed mixture into at least one guard bed prior to introducing the feed mixture into the simulated moving bed apparatus.

20. The process according to claim 1, further comprising:
feeding into at least one desorbent recovery process at least one raffinate stream and/or at least one extract stream.

21. The process according to claim 20, wherein the at least one desorbent recovery process is chosen from evaporation, distillation, crystallization, vacuum crystallization, and cooling crystallization.

22. The process according to claim 1, further comprising:
feeding into at least one water recovery process at least one raffinate stream.

23. The process according to claim 22, wherein the at least one water recovery process is chosen from evaporation, distillation, vacuum distillation, filtration, membrane separation, crystallization, evaporative crystallization, and cooling crystallization.

* * * * *